(12) United States Patent
Li et al.

(10) Patent No.: US 9,126,991 B2
(45) Date of Patent: Sep. 8, 2015

(54) RADEZOLID SALTS AND POLYMORPHIC FORMS THEREOF

(71) Applicants: Hui-Yin Li, Hockessin, DE (US); Qun Li, Newark, DE (US); Bayou Mi, Wilmington, DE (US)

(72) Inventors: Hui-Yin Li, Hockessin, DE (US); Qun Li, Newark, DE (US); Bayou Mi, Wilmington, DE (US)

( * ) Notice: Subject to any disclaimer, the term of this patent is extended or adjusted under 35 U.S.C. 154(b) by 87 days.

(21) Appl. No.: 13/998,122

(22) Filed: Oct. 2, 2013

(65) Prior Publication Data

US 2014/0100254 A1    Apr. 10, 2014

Related U.S. Application Data

(60) Provisional application No. 61/744,932, filed on Oct. 4, 2012.

(51) Int. Cl.
*C07D 413/12*    (2006.01)

(52) U.S. Cl.
CPC .................................... *C07D 413/12* (2013.01)

(58) Field of Classification Search
None
See application file for complete search history.

(56) References Cited

FOREIGN PATENT DOCUMENTS

| WO | WO 2005/019211 | 3/2005 |
|----|----------------|--------|
| WO | WO 2006/133397 | 12/2006 |

OTHER PUBLICATIONS

Jiacheng Zhou et al., Bioorganic & Medicinal Chemistry Letters, 2008 18, 6175-6176.

*Primary Examiner* — Kamal Saeed

(57) ABSTRACT

Disclosed are compounds of Formula 1a,

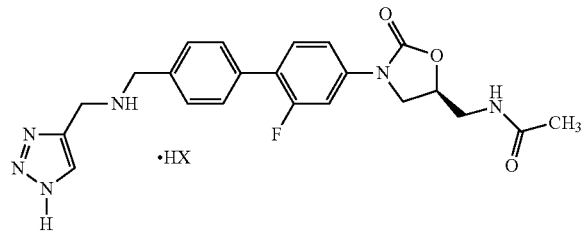

wherein HX represents HBr, phosphoric acid, sulfuric acid, methanesulfonic acid or ethanesulfonic acid, and polymorphs thereof.

7 Claims, 9 Drawing Sheets

RADEZOLID SALTS AND POLYMORPHIC FORMS THEREOF

FIELD OF THE INVENTION

This invention relates to certain salts of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide, certain polymorph forms thereof and compositions, methods of their use as therapeutic agents, and methods for their preparation.

BACKGROUND OF THE INVENTION

Oxazolidinone antibiotics are a relatively new class of antibacterial agents with activity against a broad spectrum of gram-positive pathogens. The first member of this new class to be commercialized, linezolid, was approved in 2000. Since that time the development of linezolid resistant organisms has prompted efforts to discover more effective members of the oxazolidinone class. A new family of biaryl oxazolidinone antibacterials with activity against both linezolid-susceptible and -resistant Gram-positive bacteria, as well as certain Gram-negative bacteria has been reported (see *Bioorganic & Medicinal Chemistry Letters*, 2008, 18, 6175-6178, and PCT Patent Publication WO 2005/019211). Among the known biaryloxazolidinones is N-[3-(2-fluoro-4'-{[(1H-[1,2,3]triazol-4-ylmethyl)-amino]-methyl}-biphenyl-4-yl)-2-oxo-oxazolidin-5-ylmethyl]-acetamide, more commonly known as radezolid (RX-1741), currently being developed for multi-drug-resistant infections.

Although a monohydrochloride salt of radezolid was disclosed in PCT Patent Publication WO 2006/133397, there is a continuing need for new salts and polymorphs thereof having improved properties such as solubility to optimize bioavailability on therapeutic administration.

SUMMARY OF THE INVENTION

This invention is directed to oxazolidinone salts of Formula 1a:

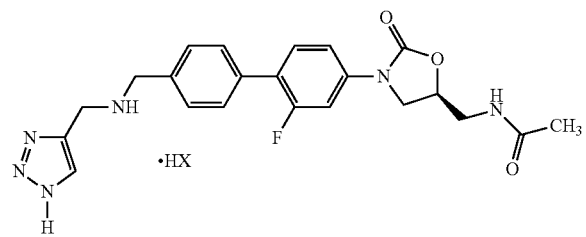

wherein HX represents HBr, phosphoric acid, sulfuric acid, methanesulfonic acid or ethanesulfonic acid.

This invention also provides polymorph forms of oxazolidinone salts of Formula 1b:

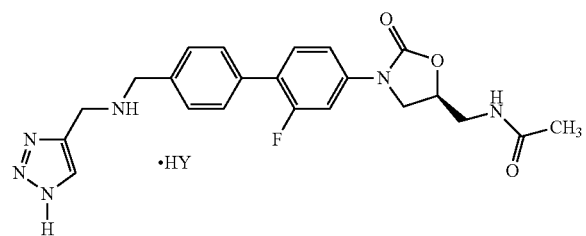

wherein HY represents HCl, HBr, phosphoric acid, sulfuric acid, methanesulfonic acid or ethanesulfonic acid. Each polymorph form is characterized by the peaks appearing in its X-ray powder diffraction (XRPD) pattern.

This invention also relates to a pharmaceutical composition comprising one or more compounds of Formula 1a (i.e., in a therapeutically effective amount) and a pharmaceutically acceptable carrier.

This invention further relates to a method of controlling a microbial infection in a mammal comprising administering to the mammal a therapeutically effective amount of a compound of Formula 1a (e.g., as a composition described herein).

This invention also provides methods for the preparation of compounds of Formula 1b.

DETAILED DESCRIPTION OF THE INVENTION

As used herein, the phrase "pharmaceutically acceptable" refers to those compounds, materials, compositions, carriers and/or dosage forms which are suitable for used in contact with the tissues of human beings and animals without excessive toxicity, irritation, allergic response, or other problems or complications, commensurate with a reasonable benefit/risk ratio.

As used herein, "mammal" refers to human and non-human patients.

As used herein, the term "effective amount of" refers to an amount of a compound, or a combination of compounds, of the present invention effective when administered alone or in combination as an anti-infective agent.

The term crystalline "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph can exhibit beneficial effects (e.g., suitability for preparation of useful formulations, improved solubility, etc.), relative to another polymorph or a mixture of polymorphs of the same compound. Preparation and isolation of a particular polymorph of a compound can be achieved by methods known to those skilled in the art including, for example, crystallization using selected solvents and temperatures.

Embodiments of the present invention as described in the Summary of the Invention include:

Embodiment 1

The polymorph of a compound of Formula Ib wherein HY represents HCl, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrochloride.

Embodiment 2

The polymorph of Embodiment 1 wherein said polymorph is in the form of a crystalline polymorph that exhibits an X-ray powder diffraction pattern having characteristic peaks, expressed in degrees 2θ, as shown in Table 1.

Embodiment 3

Figure 1:
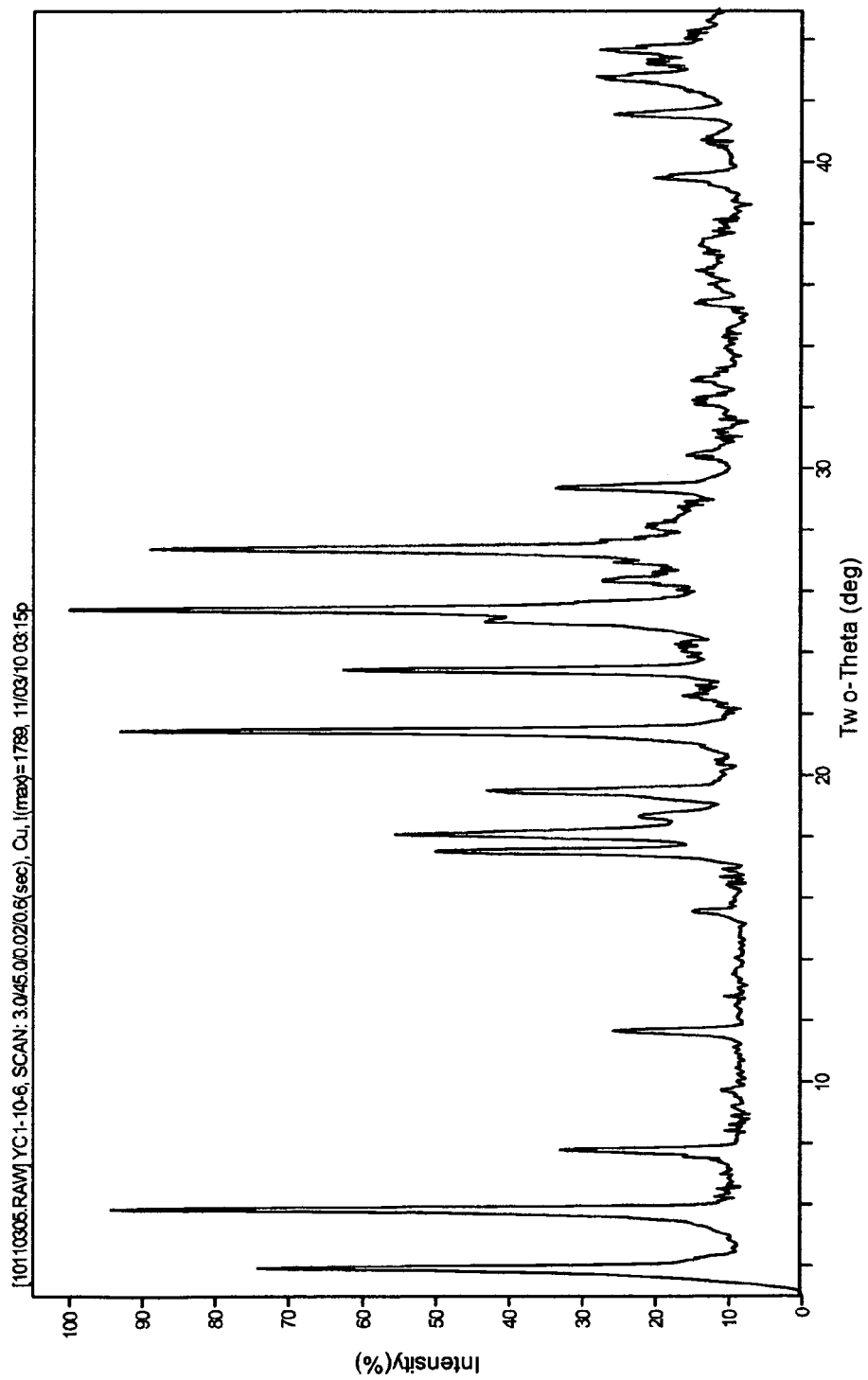
FIG. 1 shows a characteristic X-ray powder diffraction (XRPD) pattern of a crystalline polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrochloride.

The polymorph of Embodiment 1 wherein said polymorph is in the form of a crystalline polymorph that exhibits an X-ray powder diffraction pattern as exemplified in FIG. 1.

Embodiment 4

The polymorph of a compound of Formula Ib wherein HY represents HBr, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide.

Embodiment 5

The polymorph of Embodiment 4 wherein said polymorph is in the form of a crystalline polymorph that exhibits an X-ray powder diffraction pattern having characteristic peaks, expressed in degrees 2θ, as shown in Table 2.

Embodiment 6

Figure 2:
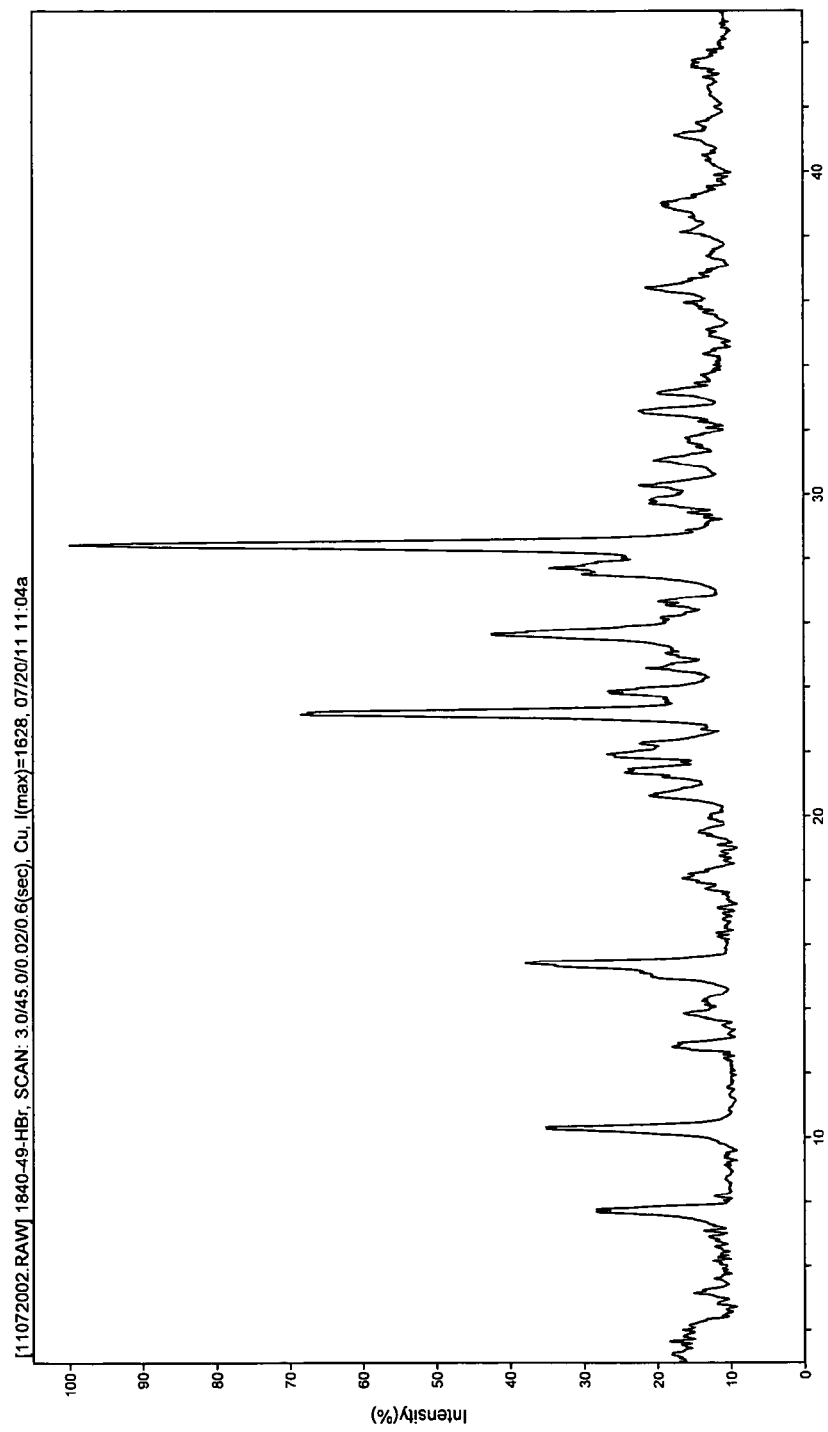
FIG. 2 shows a characteristic XRPD pattern of a crystalline polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide.

The polymorph of Embodiment 4 wherein said polymorph is in the form of a crystalline polymorph that exhibits an X-ray powder diffraction pattern as exemplified in FIG. 2.

Embodiment 7

Figure 3:
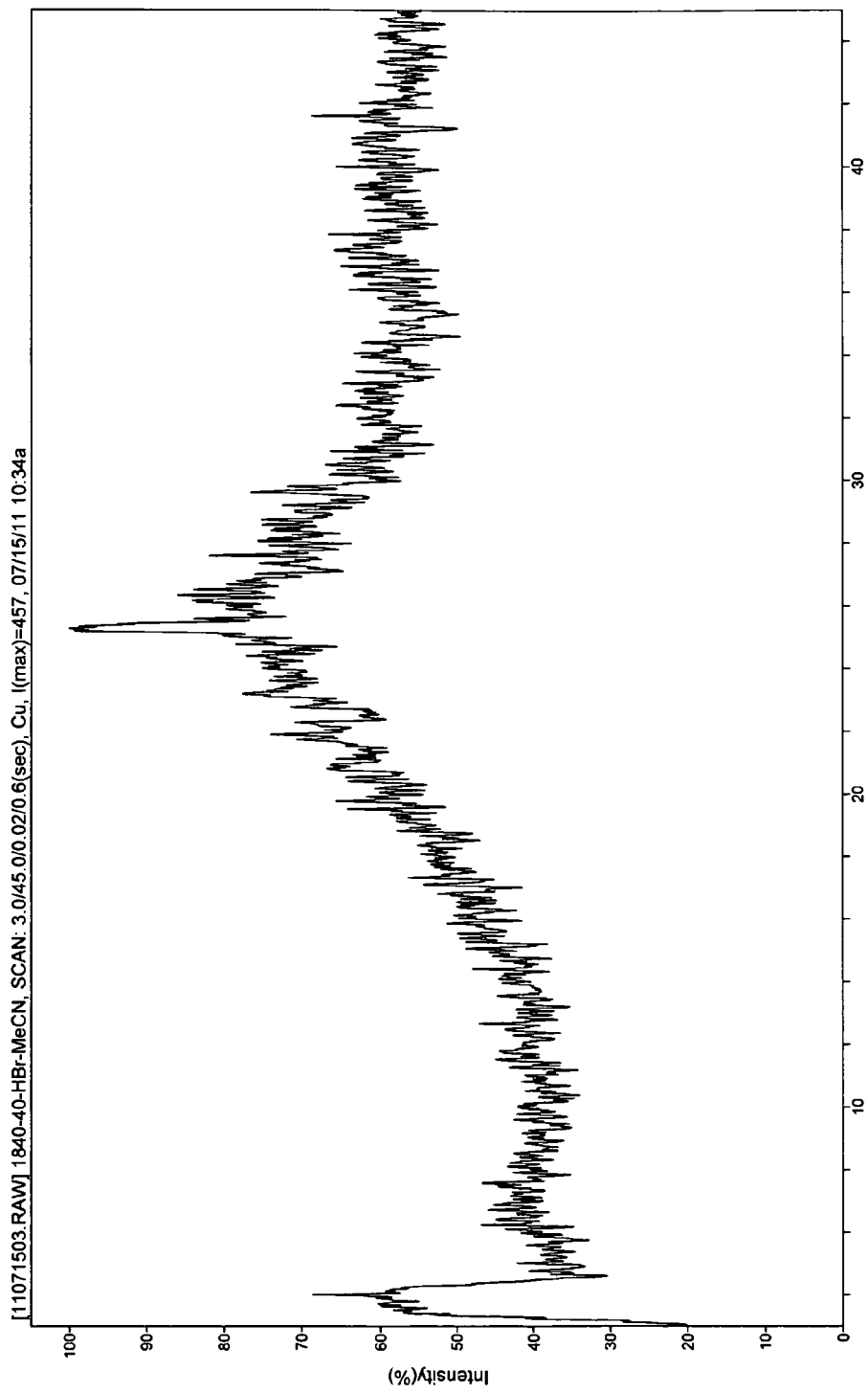
FIG. 3 shows a characteristic XRPD pattern of an amorphous polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide.

The polymorph of Embodiment 4 wherein said polymorph is in the form of an amorphous polymorph that exhibits an X-ray powder diffraction pattern as exemplified in FIG. 3.

Embodiment 8

The polymorph of a compound of Formula Ib wherein HY is phosphoric acid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate.

Embodiment 9

The polymorph of Embodiment 8 wherein said polymorph is in the form of a crystalline polymorph that exhibits an X-ray powder diffraction pattern having characteristic peaks, expressed in degrees 2θ, as shown in Table 3.

Embodiment 10

Figure 4:
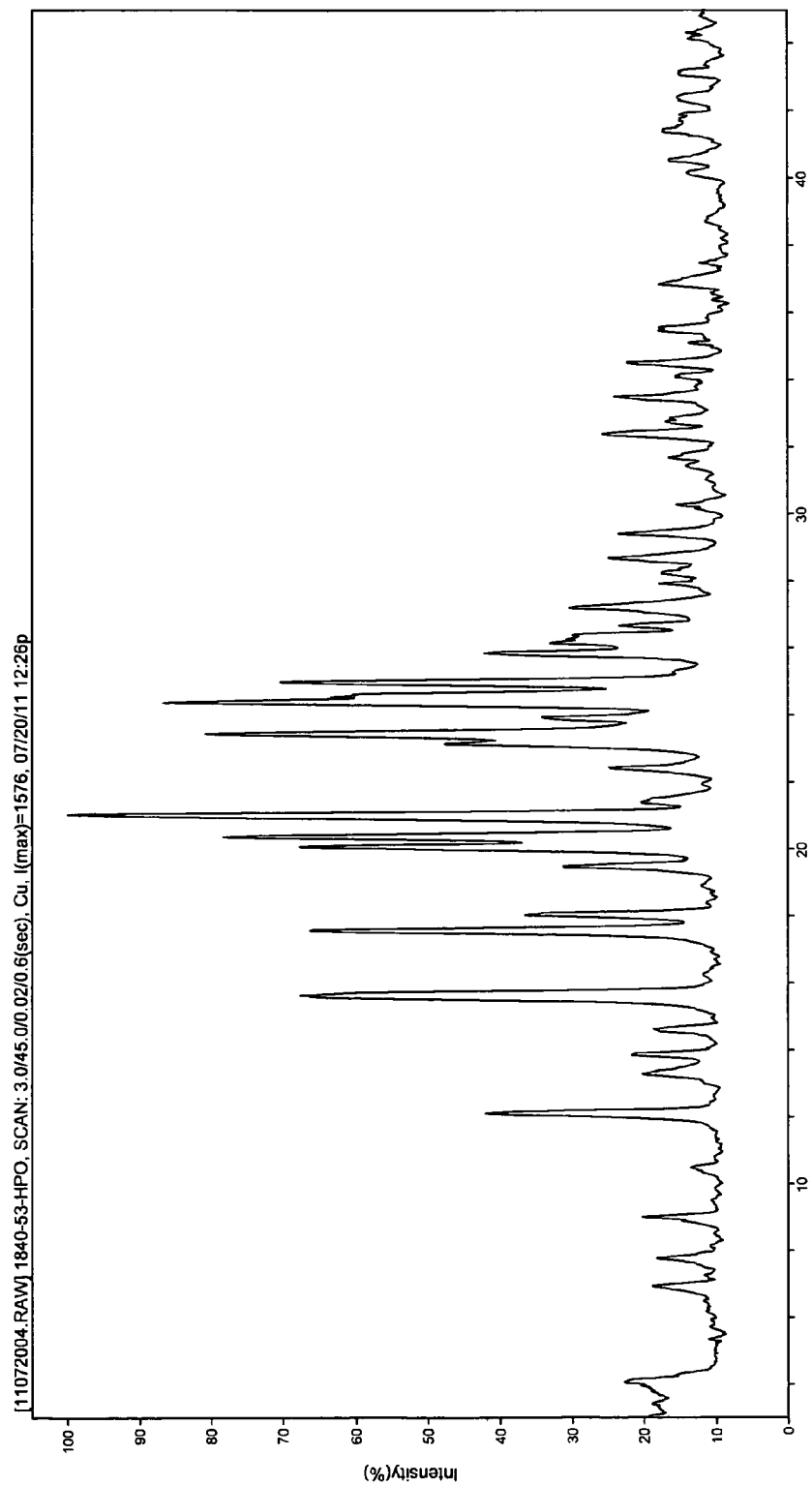
FIG. 4 shows a characteristic XRPD pattern of a crystalline polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate.

The polymorph of Embodiment 8 wherein said polymorph is in the form of a crystalline polymorph that exhibits an X-ray powder diffraction pattern as exemplified in FIG. 4

Embodiment 11

Figure 5:
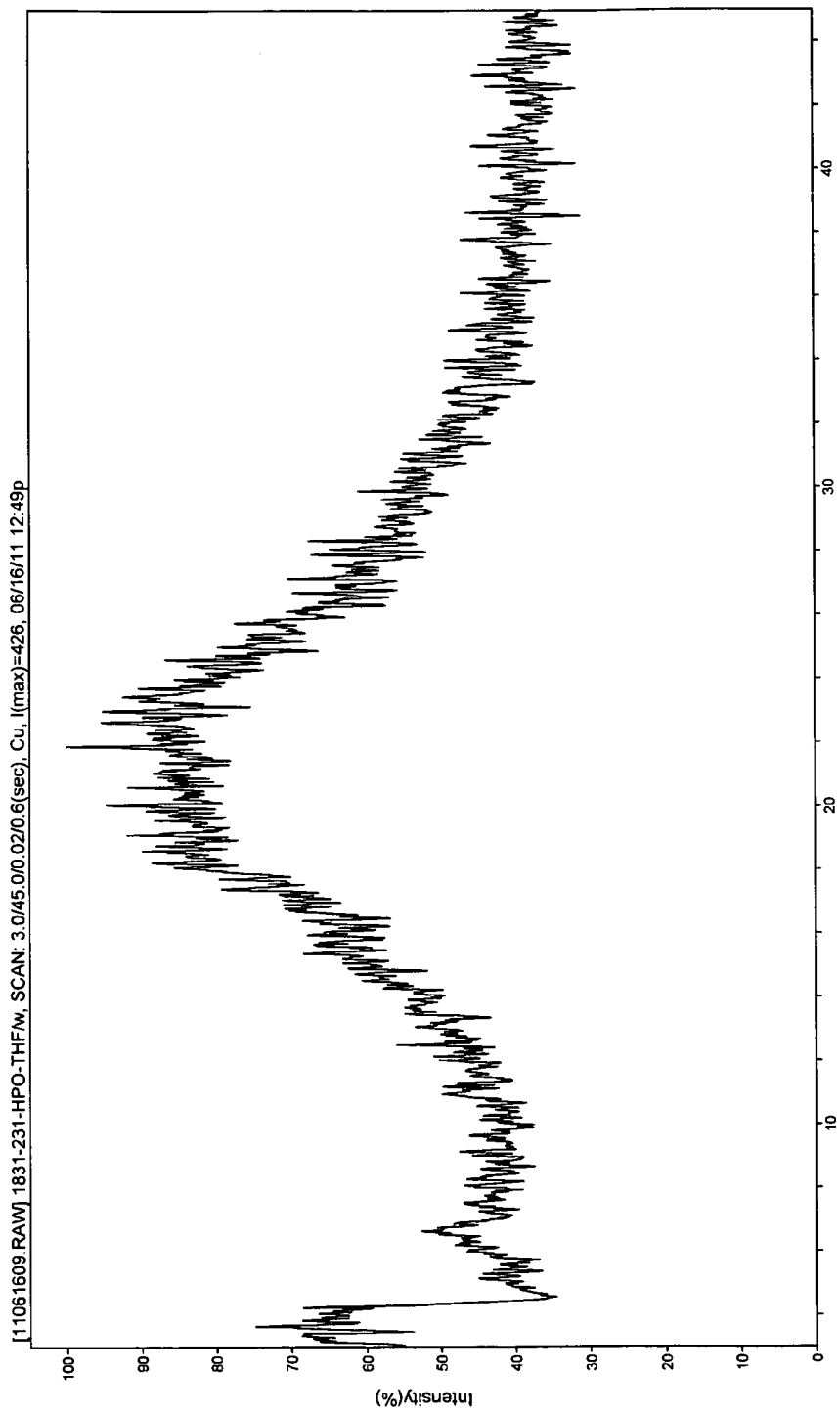
FIG. 5 shows a characteristic XRPD pattern of an amorphous polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate.

The polymorph of Embodiment 8 wherein said polymorph is in the form of an amorphous polymorph that exhibits an X-ray powder diffraction pattern as exemplified in FIG. 5.

Embodiment 12

The polymorph of a compound of Formula Ib wherein HY is phosphoric acid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate.

Embodiment 13

The polymorph of Embodiment 12 wherein said polymorph is in the form of a crystalline polymorph that exhibits an X-ray powder diffraction pattern having characteristic peaks, expressed in degrees 2θ, as shown in Table 4.

Embodiment 14

Figure 6:
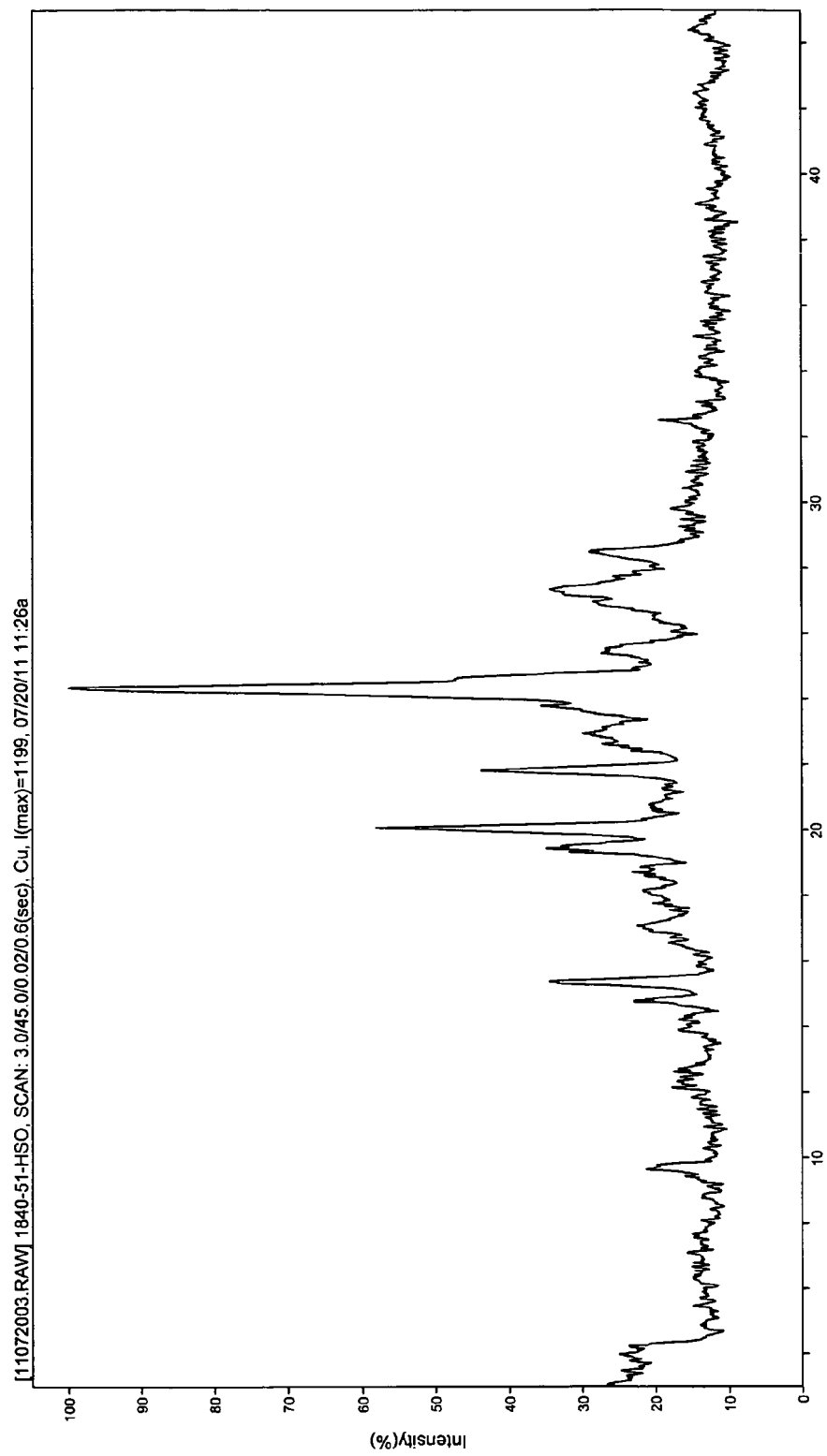
FIG. 6 shows a characteristic XRPD pattern of a crystalline polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate.

The polymorph of Embodiment 12 wherein said polymorph is in the form of a crystalline polymorph that exhibits an X-ray powder diffraction pattern as exemplified in FIG. 6.

Embodiment 15

Figure 7:
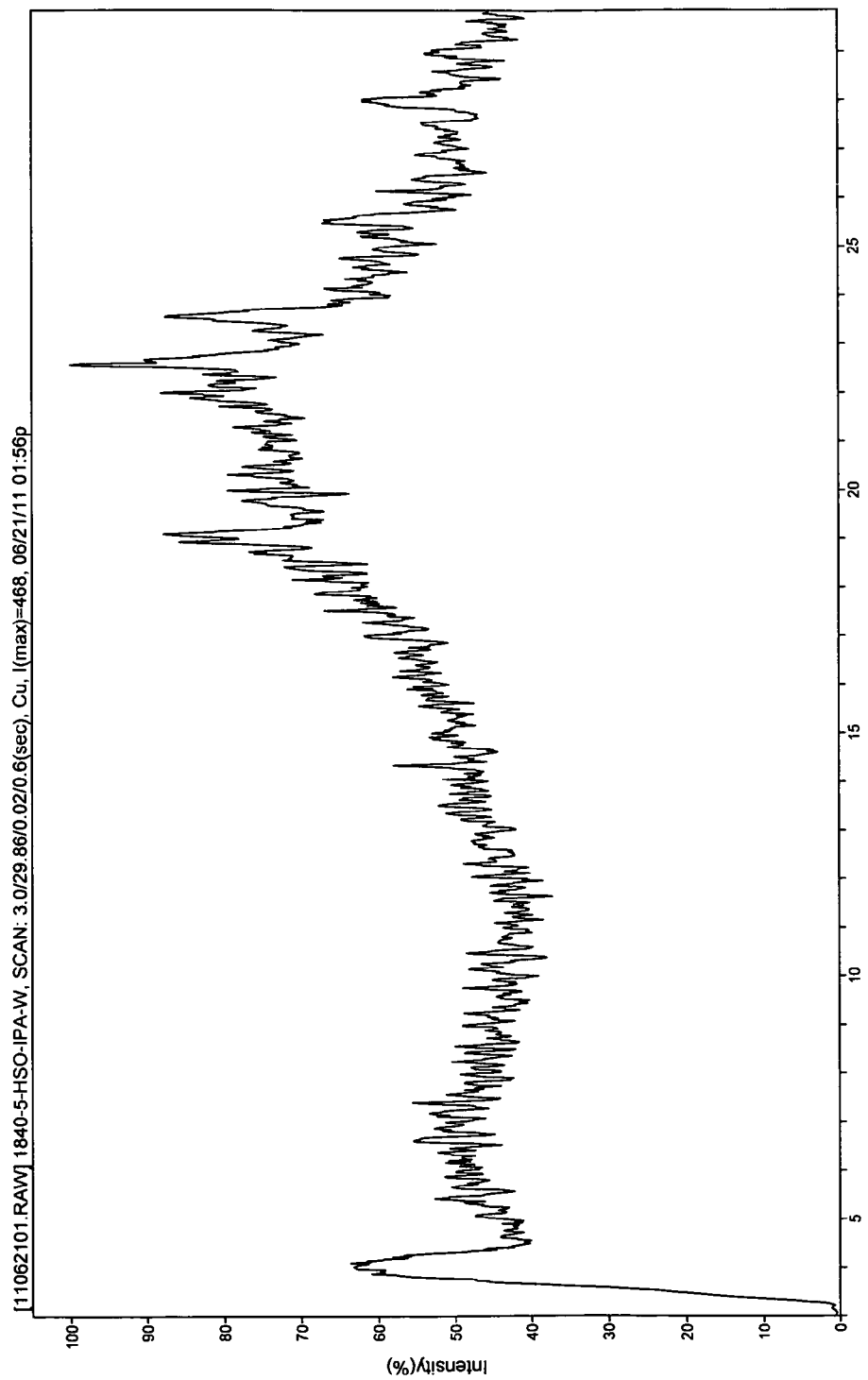
FIG. 7 shows a characteristic XRPD pattern of an amorphous polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate.

The polymorph of Embodiment 12 wherein said polymorph is in the form of an amorphous polymorph that exhibits an X-ray powder diffraction pattern as exemplified in FIG. 7.

Embodiment 16

The polymorph of a compound of Formula Ib wherein HY is methanesulfonic acid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monomethanesulfonate.

Embodiment 17

The polymorph of Embodiment 16 wherein said polymorph is a crystalline polymorph that exhibits an X-ray pow-

Embodiment 18

Figure 8:
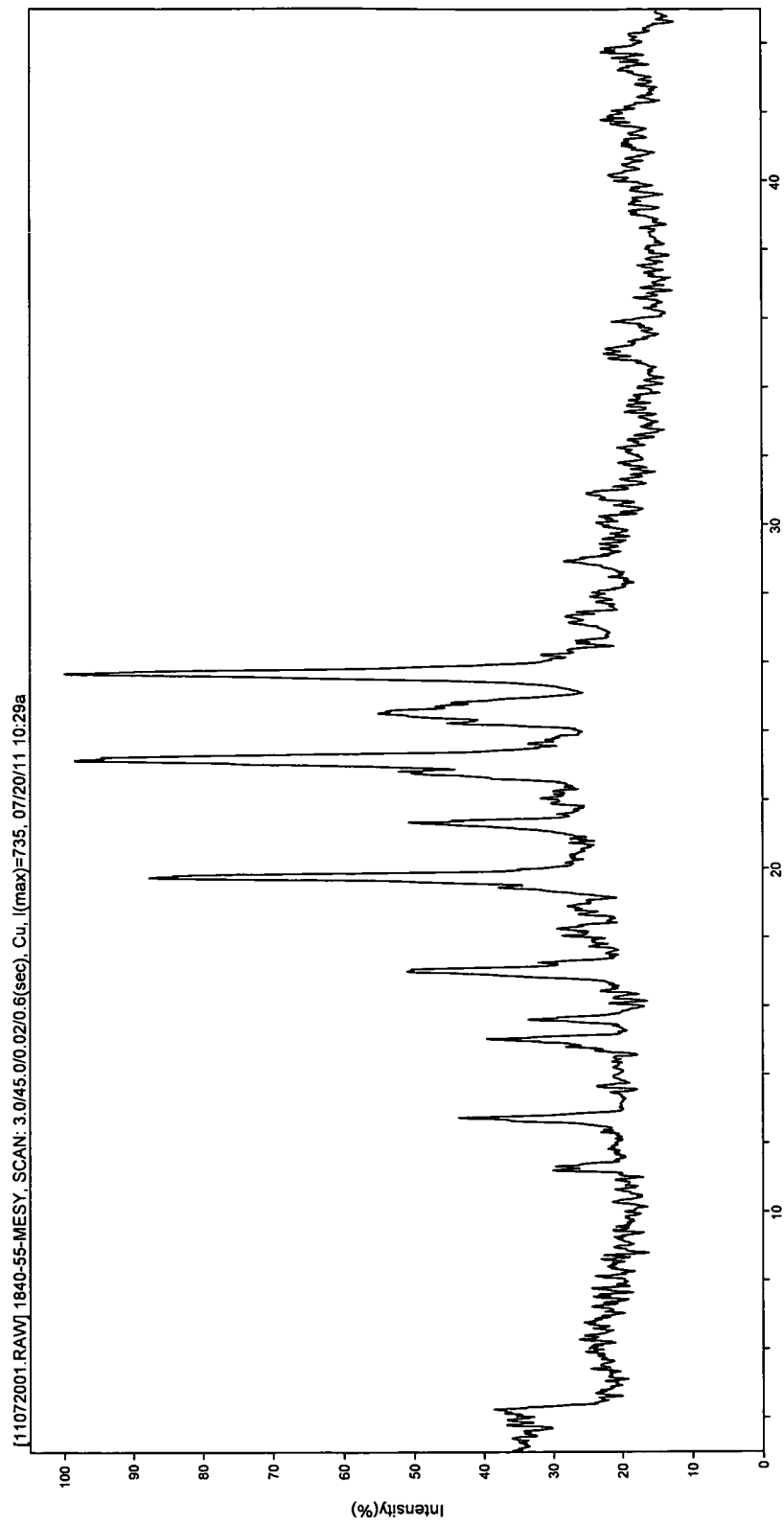
FIG. 8 shows a characteristic XRPD pattern of a crystalline polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monomethanesulfonate.

The polymorph of Embodiment 16 wherein said polymorph is in the form of a crystalline polymorph that exhibits an X-ray powder diffraction pattern as exemplified in FIG. 8.

Embodiment 19

A polymorph of Formula 1b wherein HY is ethanesulfonic acid, N-{[(5S)-3-(2-fluoro-4 {[(1H-1,2,3-triazol-5-ylmethyl)amino]methyl}biphenyl-4-yl)-2-oxo-1,3-oxazolidin-5-yl]methyl}acetamide monoethanesulfonate

Embodiment 20

The polymorph of Embodiment 19 wherein said polymorph is a crystalline polymorph that exhibits an X-ray powder diffraction pattern having characteristic peaks, expressed in degrees 2θ, as shown in Table 6.

Embodiment 21

Figure 9:
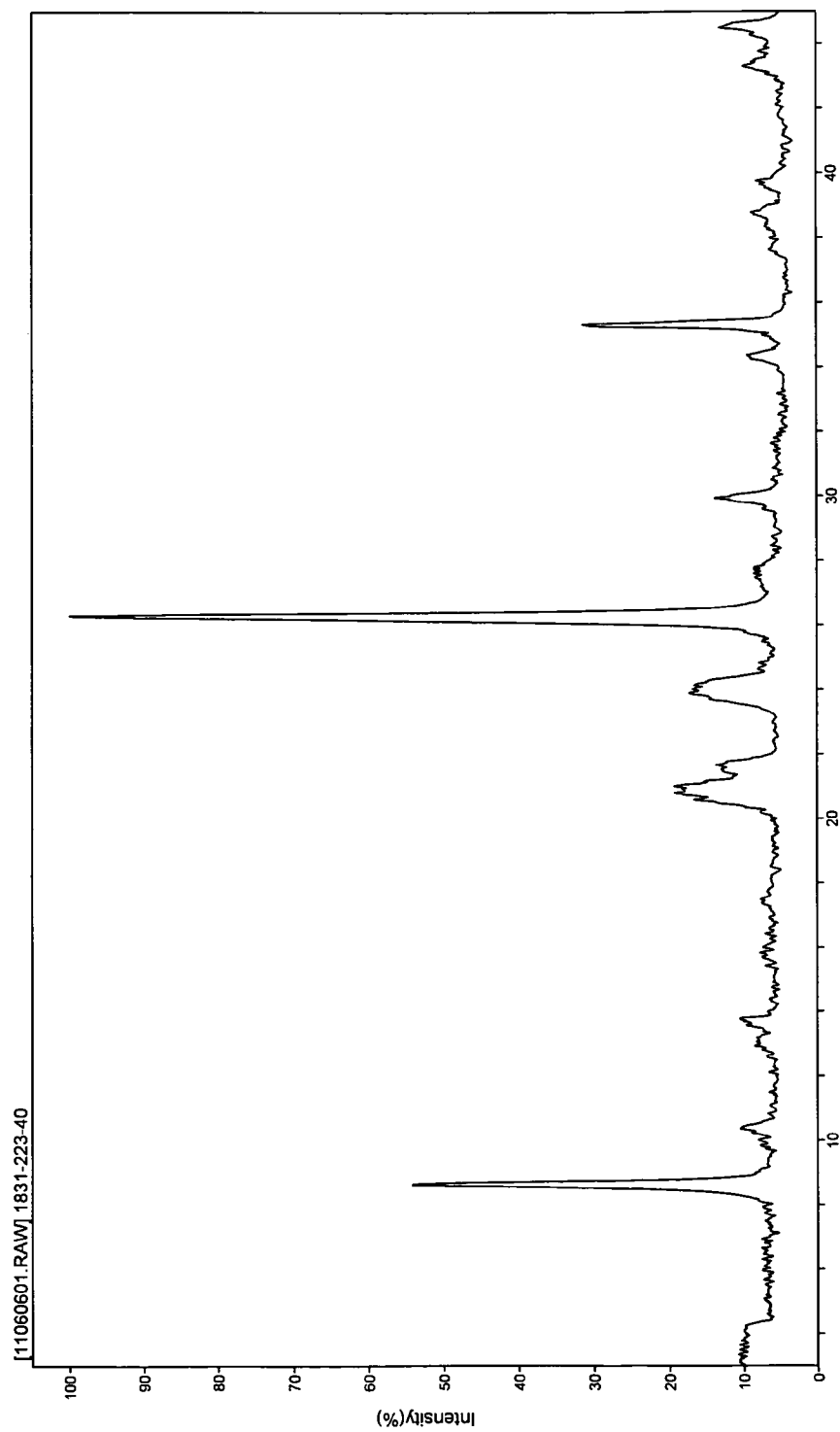
FIG. 9 shows a characteristic XRPD pattern of a crystalline polymorph form of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monoethanesulfonate.

A polymorph of Embodiment 19 wherein said polymorph is in the form of a crystalline polymorph that exhibits an X-ray powder diffraction pattern as exemplified in FIG. 9.

This invention provides a pharmaceutical composition comprising one or more compounds of Formula 1a and a pharmaceutically acceptable carrier. Of note as embodiments of such compositions are compositions comprising a compound corresponding to any of the embodiments described above.

This invention provides a method of controlling a microbial infection in a mammal comprising administering to the mammal a therapeutically effective amount of a compound of Formula 1a. Of note as embodiment of such methods are methods comprising applying a therapeutically effective amount of a compound corresponding to any of the embodiments described above. Of particular note are embodiments where compounds are applied as compositions of this invention. Also of particular note are embodiments where compounds are administered orally, parenterally or topically.

The present invention further discloses a method for preparing polymorphic forms of a compound of Formula 1b from radezolid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide, a compound of Formula 2,

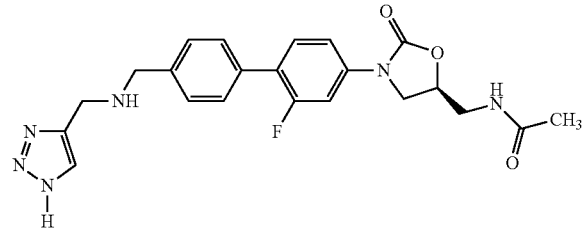

2 and hydrogen bromide, phosphoric acid, sulfuric acid, methanesulfonic acid or ethanesulfonic acid, comprising:
A) suspending the compound of Formula 2 in a suitable first solvent to form a slurry;
B) dissolving a corresponding acid HY is a suitable second solvent to form solution B;
C) adding solution B to slurry A or vice versa to form a reaction mixture;
D) separating the resulting solid, i.e., a compound of Formula 1, from the reaction mixture.

The first and second solvents are independently selected from the group consisting of water, methanol, ethanol, isopropanol, dichloromethane, ethyl acetate and acetonitrile.

The polymorph salts of the present invention (i.e., a compound of Formula 1b) may be in a non-solvated form or a solvated form, in particular in a hydrated form or an alcoholated form.

The polymorph salts of the present invention (i.e., a compound of Formula 1b) may be in an amorphous form or in various crystalline forms thereof, or in a form of a mixture of these forms.

Polymorph forms of the present invention are characterized by the peaks appearing in the X-ray powder diffraction (XRPD) pattern. The XRPD patterns of the polymorphs of this invention were measured by a Rigaku Miniflex X-ray Powder Diffractometer (XRPD) instrument.

X-ray radiation is from Copper (Cu) at 1.054056 Å with a $K_\beta$ filter. X-ray power is 30 KV, 15 mA. Sample powder is dispersed on a zero-background sample holder. General measurement conditions are: start angle—3; stop angle—45; scan speed—2 deg/min.

Example 1

Preparation of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrochloride crystalline polymorph To a stirred suspension of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide (3.5 g, 7.75 mmol) in methanol (4 mL) and ethyl acetate (17.5 mL) was added 4.0 N hydrogen chloride in dioxane (8.0 mL). The resulting mixture was stirred for 8 h, the solvent removed under reduced pressure and the residue dried in vacuo. The residue was suspended in 10% methanol in acetonitrile (17.5 mL) and stirred at room temperature for 1 h. The solid was filtered, washed with 10% methanol in acetonitrile (17.5 mL) and dried under reduced pressure at 45° C. to afford the title compound (3.32 g, 90.2%) as a crystalline solid which was characterized by XRPD. FIG. 1 shows a characteristic X-ray powder diffraction (XRPD) pattern of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrochloride. Characteristic peaks, expressed in degrees 2θ, are listed in Table 1.

TABLE 1

| Angle 2θ [°] | Relative Intensity (%) |
| --- | --- |
| 3.92 | 87.2 |
| 5.84 | 99.8 |
| 7.78 | 28.4 |
| 11.659 | 20.7 |
| 17.501 | 41.5 |
| 18.06 | 53.2 |
| 18.641 | 10.5 |
| 19.498 | 37.7 |
| 21.421 | 97.9 |
| 23.419 | 58.4 |

TABLE 1-continued

| Angle 2θ [°] | Relative Intensity (%) |
| --- | --- |
| 25 | 33.7 |
| 25.381 | 100 |
| 27.36 | 83.8 |
| 29.342 | 25.1 |
| 39.48 | 12.9 |
| 41.559 | 17.5 |
| 42.759 | 13.8 |
| 43.219 | 8.4 |
| 43.66 | 15.3 |

Example 2

Preparation of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide crystalline polymorph To a stirred suspension of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide (56.7 mg, 0.129 mmol) in ethanol (1.0 mL) was added 1.0 M hydrogen bromide in ethanol containing 8.77% water (0.39 mL, 0.39 mmol), and the resulting mixture was stirred at room temperature for 60 min. The mixture was then heated to 65° C., stirred for 60 min, cooled to room temperature and stirred for an additional 2 h. The solid was filtered and dried under reduced pressure at 50° C. to afford the title compound (64.5 mg, 94.5%) as a crystalline solid which was characterized by XRPD. FIG. 2 shows a characteristic X-ray powder diffraction (XRPD) pattern of crystalline N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide. Characteristic peaks, expressed in degrees 2θ, are listed in Table 2.

TABLE 2

| Angle 2θ [°] | Relative Intensity (%) |
| --- | --- |
| 7.701 | 21 |
| 10.338 | 30.8 |
| 13.859 | 7.7 |
| 14.24 | 4.4 |
| 15.421 | 32.9 |
| 18.06 | 8.3 |
| 21.341 | 10.8 |
| 21.92 | 16.2 |
| 23.161 | 66.5 |
| 23.879 | 15.3 |
| 25.639 | 33 |
| 27.681 | 22.5 |
| 28.42 | 100 |
| 29.701 | 10.4 |
| 30.277 | 11.9 |
| 31.042 | 10 |
| 32.579 | 12.5 |
| 33.142 | 9.9 |
| 36.418 | 13 |
| 39.021 | 9.1 |
| 41.121 | 7.6 |

Example 3

Preparation of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide amorphous polymorph To a suspension of N-[3-(2-Fluoro-4'-{[(1H-[1,2,3]triazol-4-ylmethyl)-amino]-methyl}-biphenyl-4-yl)-2-oxo-oxazolidin-5-ylmethyl]-acetamide (20 mg, 0.046 mmol) in 1:1 methanol/dichloromethane (0.6 mL) was added dropwise 0.5 M hydrobromic acid in isopropanol (0.28 mL, 0.14 mmol). The reaction mixture was stirred overnight at room temperature. The solvent was removed under reduced pressure, acetonitrile (0.6 mL) was added and the resulting slurry stirred at room temperature overnight. The solid was filtered and dried to give the title compound (0.6 g, 98%) as a solid which was characterized by XRPD. FIG. 3 shows a characteristic X-ray powder diffraction (XRPD) pattern of amorphous N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide.

Example 4

Preparation of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate crystalline polymorph To a stirred suspension of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide (50.69 mg, 0.116 mmol) in ethanol (1.0 mL) and dichloromethane (0.6 mL) was added 0.5 M phosphoric acid in isopropanol (0.6 mL, 0.30 mmol), and the resulting mixture stirred at room temperature for 10 min. The solvent volume was reduced to about 0.7 mL, ethanol (0.9 mL) was added, and the resulting mixture was refluxed for 20 min. The mixture was cooled to room temperature and stirred for an additional 2 h. The resulting solid was filtered, washed with methyl tert-butyl ether (0.6 mL) and dried under reduced pressure at 50° C. to afford the title compound (69.1 mg, 94.2%) as a crystalline solid which was characterized by XRPD. FIG. 4 shows a characteristic X-ray powder diffraction (XRPD) pattern of crystalline N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate. Characteristic peaks, expressed in degrees 2θ, are listed in Table 3.

TABLE 3

| Angle 2θ [°] | Relative Intensity (%) |
| --- | --- |
| 6.938 | 9.9 |
| 9 | 12.7 |
| 12.101 | 38.3 |
| 13.281 | 12.2 |
| 13.843 | 13.7 |
| 15.62 | 67.9 |
| 17.56 | 66.5 |
| 18.022 | 31 |
| 19.479 | 21 |
| 20.36 | 74.7 |
| 21.02 | 100 |
| 22.435 | 15.2 |
| 23.439 | 75.6 |
| 23.935 | 16.3 |
| 24.362 | 79.2 |
| 24.98 | 64.4 |
| 25.841 | 34.4 |
| 26.178 | 21.5 |
| 27.201 | 20.9 |
| 27.921 | 7.6 |
| 28.679 | 16.9 |
| 29.401 | 16 |
| 32.379 | 17.4 |
| 33.497 | 15 |
| 34.083 | 6.2 |
| 35.461 | 10.5 |
| 36.842 | 10.9 |

TABLE 3-continued

| Angle 2θ [°] | Relative Intensity (%) |
|---|---|
| 40.557 | 8.4 |
| 41.381 | 8.5 |
| 41.881 | 6.4 |

Example 5

Preparation of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate amorphous polymorph To a stirred suspension of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide (50.69 mg, 0.116 mmol) in isopropanol (1.0 mL) was added 0.5 M phosphoric acid in isopropanol (0.7 mL, 0.35 mmol), and the resulting mixture stirred at room temperature for 20 min. The resulting stirred suspension was heated to 80° C. and then concentrated under reduced pressure to give a solid. The solid was treated with aqueous tetrahydrofuran, stirred, and concentrated under reduced pressure to give the title compound as an amorphous solid which was characterized by XRPD. FIG. 5 shows a characteristic X-ray powder diffraction (XRPD) pattern of amorphous N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate.

Example 6

Preparation of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate crystalline polymorph To a stirred suspension of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide (50.5 mg, 0.115 mmol) in methanol (1.2 mL) was added 0.5 M sulfuric acid in isopropanol (0.64 mL, 0.32 mmol) and the resulting mixture heated to 55° C. to give an almost clear solution. The resulting mixture was cooled to room temperature and stirred for an additional 2 h. The resulting solid was filtered, washed with methyl tert-butyl ether (0.5 mL) and dried under reduced pressure at 50° C. to afford the title compound (48 mg, 77.7%) as a crystalline solid which was characterized by XRPD. FIG. 6 shows a characteristic X-ray powder diffraction (XRPD) pattern of crystalline N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate. Characteristic peaks, expressed in degrees 2θ, are listed in Table 4.

TABLE 4

| Angle 2θ [°] | Relative Intensity (%) |
|---|---|
| 4.22 | 8.8 |
| 9.641 | 11.7 |
| 12.32 | 5.6 |
| 12.618 | 6.1 |
| 14.78 | 13.1 |
| 15.398 | 27.9 |
| 16.56 | 4.8 |
| 17.08 | 8.9 |
| 18.157 | 5.8 |
| 19.46 | 22.3 |
| 20.08 | 51.3 |
| 21.821 | 34 |
| 23.016 | 9.2 |
| 24.34 | 100 |
| 25.44 | 10.2 |
| 26.901 | 10.1 |
| 27.36 | 18.9 |
| 28.501 | 14 |

Example 7

Preparation of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate amorphous polymorph To a stirred suspension of N-[3-(2-Fluoro-4'-{[(1H-[1,2,3]triazol-4-ylmethyl)-amino]-methyl}-biphenyl-4-yl)-2-oxo-oxazolidin-5-ylmethyl]-acetamide (49 mg, 0.11 mmol) in 4:1 isopropanol/water (0.8 mL) was added dropwise 0.5 M sulfuric acid in isopropanol (0.65 mL, 0.33 mmol). The mixture was then stirred for 2 h and the solvent removed under reduced pressure to give the title compound as an amorphous off-white solid which was characterized by XRPD. FIG. 7 shows a characteristic X-ray powder diffraction (XRPD) pattern of amorphous N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate.

Example 8

Preparation of the methanesulfonic acid salt of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide crystalline polymorph To a stirred suspension of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide (21.4 mg, 0.049 mmol) in methanol (0.4 mL) was added 0.5 M methanesulfonic acid in isopropyl alcohol (0.27 mL, 0.135 mmol). The resulting clear solution was stirred for 100 min to afford a slurry. The resulting solid was filtered and dried at 50° C. under reduced pressure overnight to afford the title compound (24.1 mg, 92.4%) as a crystalline solid which was characterized by XRPD. FIG. 8 shows a characteristic X-ray powder diffraction (XRPD) pattern of crystalline N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monomethanesulfonate. Characteristic peaks, expressed in degrees 2θ, are listed in Table 5.

TABLE 5

| Angle 2θ [°] | Relative Intensity (%) |
|---|---|
| 12.739 | 31.6 |
| 15.037 | 27.9 |
| 17.002 | 41.4 |
| 19.722 | 85.9 |
| 21.337 | 32.4 |
| 22.744 | 25.4 |
| 23.14 | 95.6 |

TABLE 5-continued

| Angle 2θ [°] | Relative Intensity (%) |
| --- | --- |
| 24.501 | 38.6 |
| 25.66 | 100 |
| 43.742 | 11.1 |

Example 9

Preparation of ethylenesulfonic acid salt of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide crystalline polymorph To a stirred suspension of N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide (18.52 mg, 0.042 mmol) in 1:1 methanol/dichloromethane (1.2 mL) was added 0.5 M ethanesulfonic acid in isopropyl alcohol (0.0.95 mL, 0.048 mmol). The resulting mixture was stirred and then concentrated under reduced pressure. The residue was diluted with methanol (0.08 mL), 0.5 M ethanesulfonic acid in isopropanol (0.14 mL, 0.07 mmol) added and the resulting mixture stirred overnight at room temperature. The clear solution was diluted with methyl tert-butyl ether (0.8 mL) and the mixture stirred overnight to afford a slurry. The resulting solid was filtered and dried under reduced pressure to afford the title compound as a crystalline solid which was characterized by XRPD. FIG. 9 shows a characteristic X-ray powder diffraction (XRPD) pattern of crystalline N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monoethanesulfonate. Characteristic peaks, expressed in degrees 2θ, are listed in Table 6.

TABLE 6

| Angle 2θ [°] | Relative Intensity (%) |
| --- | --- |
| 8.622 | 51.3 |
| 10.362 | 4.7 |
| 13.06 | 2.5 |
| 13.742 | 4.6 |
| 15.82 | 2.3 |
| 17.483 | 2.2 |
| 21 | 14.2 |
| 21.66 | 8.8 |
| 24.159 | 11.1 |
| 26.279 | 100 |
| 27.78 | 2.7 |
| 29.921 | 9.4 |
| 31.637 | 1.7 |
| 34.358 | 4.7 |
| 35.318 | 28.6 |
| 38.779 | 3.7 |
| 39.641 | 2.9 |
| 43.299 | 4.5 |

What is claimed is:

1. A polymorph of a compound of Formula 1b,

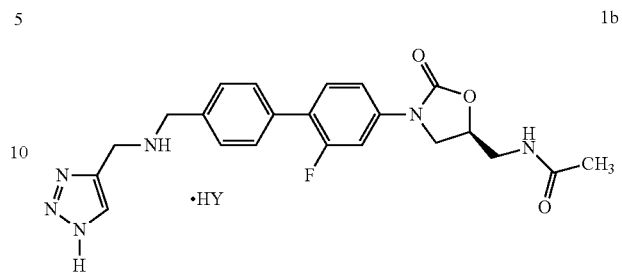

1b wherein HY represents HCl, HBr, phosphoric acid, sulfuric acid, methanesulfonic acid or ethanesulfonic acid.

2. The polymorph of claim 1 wherein HY is HCl, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrochloride, in the form of a crystalline polymorph that exhibits an X-ray powder diffraction pattern having at least the 2θ reflection positions

| 2θ |
| --- |
| 3.92 |
| 5.84 |
| 7.78 |
| 11.659 |
| 17.501 |
| 18.06 |
| 18.641 |
| 19.498 |
| 21.421 |
| 23.419 |
| 25 |
| 25.381 |
| 27.36 |
| 29.342 |
| 39.48 |
| 41.559 |
| 42.759 |
| 43.219 |
| 43.66. |

3. The polymorph of claim 1 wherein HY is HBr, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monohydrobromide, in the form of a crystalline polymorph that exhibits an X-ray powder diffraction pattern having at least the 2θ reflection positions

| 2θ |
| --- |
| 7.701 |
| 10.338 |
| 13.859 |
| 14.24 |
| 15.421 |
| 18.06 |
| 21.341 |
| 21.92 |
| 23.161 |
| 23.879 |
| 25.639 |
| 27.681 |
| 28.42 |
| 29.701 |
| 30.277 |
| 31.042 |
| 32.579 |

| 2θ |
|---|
| 33.142 |
| 36.418 |
| 39.021 |
| 41.121. |

4. The polymorph of claim 1 wherein HY is phosphoric acid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monophosphate, in the form of a crystalline polymorph that exhibits an X-ray powder diffraction pattern having at least the 2θ reflection positions

| 2θ |
|---|
| 6.938 |
| 9 |
| 12.101 |
| 13.281 |
| 13.843 |
| 15.62 |
| 17.56 |
| 18.022 |
| 19.479 |
| 20.36 |
| 21.02 |
| 22.435 |
| 23.439 |
| 23.935 |
| 24.362 |
| 24.98 |
| 25.841 |
| 26.178 |
| 27.201 |
| 27.921 |
| 28.679 |
| 29.401 |
| 32.379 |
| 33.497 |
| 34.083 |
| 35.461 |
| 36.842 |
| 40.557 |
| 41.381 |
| 41.881. |

5. The polymorph of claim 1 wherein HY is sulfuric acid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monosulfate, in the form of a crystalline polymorph that exhibits an X-ray powder diffraction pattern having at least the 2θ reflection positions

| 2θ |
|---|
| 4.22 |
| 9.641 |
| 12.32 |
| 12.618 |
| 14.78 |
| 15.398 |
| 16.56 |
| 17.08 |
| 18.157 |
| 19.46 |
| 20.08 |
| 21.821 |
| 23.016 |
| 24.34 |
| 25.44 |
| 26.901 |
| 27.36 |
| 28.501. |

6. The polymorph of claim 1 wherein HY is methanesulfonic acid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monomethanesulfonate, in the form of a crystalline polymorph that exhibits an X-ray powder diffraction pattern having at least the 2θ reflection positions

| 2θ |
|---|
| 12.739 |
| 15.037 |
| 17.002 |
| 19.722 |
| 21.337 |
| 22.744 |
| 23.14 |
| 24.501 |
| 25.66 |
| 43.742. |

7. The polymorph of claim 1 wherein HY is ethanesulfonic acid, N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide monoethanesulfonate, in the form of a crystalline polymorph that exhibits an X-ray powder diffraction pattern having at least the 2θ reflection positions

| 2θ |
|---|
| 8.622 |
| 10.362 |
| 13.06 |
| 13.742 |
| 15.82 |
| 17.483 |
| 21 |
| 21.66 |
| 24.159 |
| 26.279 |
| 27.78 |
| 29.921 |
| 31.637 |
| 34.358 |
| 35.318 |
| 38.779 |
| 39.641 |
| 43.299. |

\* \* \* \* \*